United States Patent [19]

Woodruff

[11] Patent Number: 5,451,602
[45] Date of Patent: Sep. 19, 1995

[54] CHOLECYSTOKININ ANTAGONISTS USEFUL IN THE TREATMENT OF PANIC ATTCKS

[75] Inventor: Geoffrey N. Woodruff, Herts, United Kingdom

[73] Assignee: Warner-Lambert Company, Morris Plains, N.J.

[21] Appl. No.: 190,401

[22] Filed: Feb. 2, 1994

Related U.S. Application Data

[60] Division of Ser. No. 33,062, Mar. 17, 1993, Pat. No. 5,318,981, which is a continuation of Ser. No. 729,271, Jul. 12, 1991, abandoned.

[51] Int. Cl.⁶ .............................................. A61K 31/40
[52] U.S. Cl. ................................................... 514/419
[58] Field of Search ........................................ 514/419

[56] References Cited

U.S. PATENT DOCUMENTS 5,264,419  11/1993  Horwell et al. .................. 514/18

FOREIGN PATENT DOCUMENTS 9100274  1/1991  WIPO .
9204038  3/1992  WIPO .

OTHER PUBLICATIONS

*Annu. Rev. Pharmacol. Toxicol.*, 1991, 31:469-501, "Cholecystokinin Antagonists", G. N. Woodruff et al.
*Proc. Natl. Acad. Sci.*, vol. 87, pp. 6728-6732, Sep. 1990, "Development of a class of Selective Cholacystokinin . . . " J. Hughes et al.
*Proc. Natl. Acad. Sci.*, vol. 88, pp. 1130-1133, Feb. 1991, "Evidence for an involvement of the brain . . . " L. Singh et al.
*Arch Gen Psychiatry*, vol. 46, Jun. 1989, pp. 511-517, "Cholecystokinin Tetrapeptide Induces Panic-like Attacks in Healthy . . . ", C. de Montigny.
*Can J. Psychiatry*, vol. 35, Feb. 1990, pp. 83-85, "Cholecystokinin-Tetrapeptide Induces Panic Attacks in Patients . . . ", J. Bradwejn et al.
Ravard, S. and Dourish, C., *TIPS*, vol. 11, Jul. 1990, 271-273.
Berkow, R., et al., *The Merck Manual of Diagnosis and Therapy* 15 edition, 1987, 1502-1504.
Abelson, J., et al., *Archives of General Psychiatry*, vol. 47, No. 4, Apr. 1990, 395.
Horwell, D. C., et al., *J. of Med. Chem.* 34, No. 1, 1991, 404-414.
Hughes, J., et al., *Arzneimittel-Forschung Drug Res.* 42(1) No. 2a, 1992, 250-255.

*Primary Examiner*—Kimberly R. Jordan
*Attorney, Agent, or Firm*—Elizabeth M. Anderson

[57] ABSTRACT

Unnatural dipeptoids of α-substituted Try-Phe derivatives are useful as agents in the treatment of panic disorders. These dipeptoids are $CCK_B$ antagonists having utility in the prevention of panic attacks in patients prone to these attacks.

9 Claims, No Drawings

CHOLECYSTOKININ ANTAGONISTS USEFUL IN THE TREATMENT OF PANIC ATTCKS

This is a divisional application of U.S. Ser. No. 08/033,062 filed Mar. 17, 1993, now U.S. Pat. No. 5,318,981, which is a continuation application of U.S. Ser. No. 07/729,271, filed Jul. 12, 1991, now abandoned.

BACKGROUND OF THE INVENTION

The neuropeptide cholecystokinin-8 (CCK-8) is an important neuromodulator and neurotransmitter in the brain. There are two types of CCK receptor which are currently referred to as $CCK_A$ and $CCK_B$ receptors. The major of the CCK receptor types in brain is the $CCK_B$ receptor (Review by Woodruff & Hughes, *Annual Review of Pharmacology Toxicology* 31:469-501 (1991)).

The functional role of CCK in brain is not fully understood. Recently there has been evidence that CCK is involved in anxiety and that $CCK_B$ antagonists have an anxiolytic action in animal models of anxiety (Hughes, et al., *Proc Natnl Acad Sci*, U.S.A. 87:6728-6732 (1990)

It has recently been shown (de Montigny, C *Arch Gen Psychiatry* 46:511-517 (1989); Bradwejn J, Koszyckl, D, and Metesissian, G, *Can J Psychiatr* 35:83-85 (1990) that the injection of the tetrapeptide cholecystokinin (30-33) (CCK-4) into human volunteers or into patients suffering from panic disorder precipitates a panic attack. The tetrapeptide cholecystokinin (30-33) (CCK-4) is a substance that stimulates $CCK_B$ receptors, i.e., is a $CCK_B$ antagonist. The injection of tetrapeptide cholecystokinin (30-33) (CCK-4) into the cerebral ventricles of the brain of rats precipitates the onset of an anxiogenic reaction. This anxiogenic response can be prevented by pretreatment of the rats with the $CCK_B$ antagonist CI-988 (Sing, et al., *Proc Natnl Acad Sci* U.S.A. 88:1130-1133 (1991)).

The present invention relates to compounds known as dipeptoids and/or their pharmaceutically acceptable salts for use in the prevention of panic attacks in patients prone to these attacks. Suitable compounds are cholecystokinin (CCK)$_B$ antagonists such as [R-(R*,R*)]4-[[2-[[3-(1H-indol-3-yl)-2-methyl-1-oxo-2-[[(tricyclo[3.3.1.1$^{3,7}$]dec-2-yloxy) carbonyl]amino]propyl]amino]-1-phenylethyl]amino]-4-oxobutanoic acid (CI-988).

The compounds useful in this invention are fully described in Ser. No. 07/629,809, filed Dec. 19, 1990, now U.S. Pat. No. 5,278,316. Methods of preparing the compounds, intermediates useful in their preparation, compositions containing the compounds, and uses of the compounds are disclosed. The uses disclosed include the treatment of obesity, hypersecretion of gastric acid in the gut, gastrin-dependent tumors, psychoses, anxiety, ulcer, depression, withdrawal response produced by chronic treatment or use followed by withdrawal from nicotine, diazepam, alcohol, cocaine, caffeine, or opioids.

The disclosure of Ser. No. 07/629,809, now U.S. Pat. No. 5,278,316, is incorporated herein by reference.

SUMMARY OF THE INVENTION

The instant invention concerns a new method of treating panic disorders which comprises administering to a human in need of such treatment or therapeutically effective amount of a compound of formula

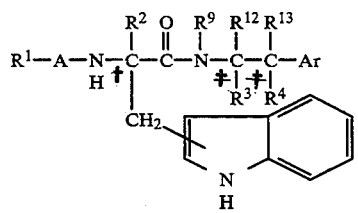

or a pharmaceutically acceptable salt thereof in unit dosage form. $R^1$, A, $R^2$, $R^3$, $R^4$, $R^9$, $R^{12}$, $R^{13}$, and Ar are as defined below.

The method of the invention is administering the compound in an amount of 0.1 to 20 mg/kg of body weight. A preferred amount is from 1 to 10 mg/kg of body weight.

Preferred compounds useful in this method are those of formula I wherein the cycloalkyl or polycycloalkyl has from about six to ten carbon atoms unsubstituted or substituted with one or more substituents, each substituent selected independently from: methyl, fluorine, chlorine, and bromine.

Other preferred compounds useful in this method are those of formula I wherein $R^1$ is cycloalkyl or polycycloalkyl wherein the polycycloalkyl is selected from the group consisting of

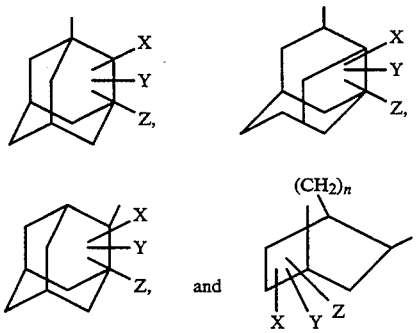

wherein W, X, Y, and Z are each independently hydrogen, a straight or branched alkyl of from one to six carbon atoms, $CF_3$, $NR^5R^6$, $-(CH_2)_nCO_2R^*$, CN, F, Cl, Br, OR*, SR*, wherein R*, $R^5$ and $R^6$ are as defined in claim 1 and n is an integer of from 1 to 3.

A is —NHCO—, OC(=O)—, —SO$_2$—, —S(=O)—, —SCO— or —CH$_2$CO—; and

Ar is 2- or 3-thienyl, 2- or 3-furanyl, 2-, 3-, or 4-pyridinyl or an unsubstituted or substituted phenyl whose substituents if any are each independently hydrogen, fluorine, chlorine, bromine, iodine, methyl, methoxy, trifluoromethyl, nitro, OH, NH$_2$, OCF$_3$, NHCOCH$_2$CH$_2$CO$_2$H, or CH$_2$CH$_2$CO$_2$H.

More preferred compounds of the instant invention are those of formula I wherein in the compound of formula I $R^1$ is 2-adamantyl or 1—(S)-2-endobornyl;
A is —NHCO—, —OCO—, —SO$_2$—, —S(=O)—, or —CH$_2$CO—;
$R^2$ is —CH$_3$, —CH$_2$CO$_2$H or —CH$_2$C≡CH;
$R^3$ is —(CH$_2$)$_n$—B—D or H;
$R^4$ is —(CH$_2$)$_n$—B—D or H; and
$R^9$ is hydrogen or methyl.

Still more preferred compounds of the invention are those of formula I wherein in the compound of formula I $R^1$ is 2-adamantyl, 1—(S)-2-endobornyl, or 2-methyl cyclohexyl,
A is —OC(=O)—;
$R^2$ is —$CH_3$;
$R^3$ is H, $CH_2OH$, $CH_2OCOCH_2CH_2CO_2H$, $CH_2O$-$COCH=CHCO_2H$, $CH_2NHCOCH_2CN_2CO_2H$, $CH_2NHCOCH=CHCO_2H$, or $CH_2CO_2H$;
$R^4$ is H, —$CH_2SCH_2CO_2H$, —$CH_2SCH_2CH_2CO_2H$, —NHCOCH=CHCO_2H, —NHCOCH_2CH_2CO_2H$ ([D] configuration) or $NHCOCH=CHCO_2H$ [(D) configuration].

Especially preferred compounds useful in preventing panic attacks or in treating the symptoms of panic are (±)-trans-2-chlorocyclohexyl [1-(1H-indol-3-ylmethyl)-1-methyl-2-oxo-2-[(2phenylethyl)amino]ethyl]carbamate;

2-chlorocyclohexyl [2-[1-(hydroxymethyl)-2-phenylethyl]-amino]-1-(1H-indol-3-ylmethyl)-1-methyl-2-oxoethyl]-carbamate;

2-[[2-[[[(2-chlorocyclohexyl)oxy]carbonyl]amino]-3-(1H-indol-3-yl)-2-methyl-1-oxopropyl]amino]-3-phenylpropyl butanedioate;

2-[[2-[[[(2-methylcyclohexyl)oxy]carbonyl]amino]-3-(1H-indol-3-yl)-2-methyl-1-oxopropyl]amino]-3-phenylpropyl butanedioate;

(±)-tricyclo[3.3.1.1$^{3,7}$]dec-2-yl[1-(1H-indol-3-ylmethyl)-1-methyl-2- oxo- 2- [(2-phenylethyl) amino]ethyl ]carbamate;

(±) or (−)-2-chlorocyclohexyl[1-(1H-indol-3-ylmethyl)-1-methyl-2-oxo-2-[(2-phenyl ethyl)amino]ethyl]carbamate;

tricyclo[3.3.1.1$^{3,7}$]dec-2-yl[2-[[1-(hydroxymethyl)-2-phenylethyl]amino]-1-(1H-indol -3-ylmethyl)-1-methyl-2-oxoethyl]carbamate;

2-[[3-(1H-indol-3-yl)-2-methyl-1-oxo-2-[[(tricyclo-[3.3.1.1$^{3,7}$]dec-2-yloxy) carbonyl]amino]propyl]amino]-3-phenylpropyl butanedioate;

[R-(R*,R*)]-4-[[2-[[3-(1H-indol-3-yl)-2-methyl-1-oxo-2-[[(tricyclo[3.3.1.1$^{37}$]dec-2-yloxy)carbonyl]amino]propyl]amino]-1-phenylethyl]-amino]-4-oxobutanoic acid;

[1S-[1α,2β[S*(S*)],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxobutanoic acid;

[R-[R*,S*-(E)]]-4-[[2-[[3-(1H-indol-3-yl)-2-methyl-1-oxo-2-[[tricyclo[3.3.1.1$^{3,7}$]dec-2-yloxy)carbonyl]amino]-propyl]amino]-3-phenylpropyl]amino]-4-oxo-2-butenoic acid;

[R-(R*,S*)]-4-[[2-[[3-(1H-indol-3-yl)-2-methyl-1-oxo-2-[[(tricyclo[3.3.1.1$^{3,7}$]dec-2-yloxy)carbonyl]amino]-propyl]amino]-3-phenylpropyl]amino]-4-oxo-butanoic acid;

(R)-tricyclo[3.3.1.1$^{3,7}$]dec-2-yl-[1-(1H-indol-3-ylmethyl)-1-methyl-2-[methyl-(2-phenylethyl) amino]-2-oxoethylcarbamate;

[R-(R*,S*)]-2-[[2-[[3-(1M-indol-3-yl)-2-methyl-1-oxo-2-[[(tricyclo[3.3.1.1$^{3,7}$]dec-2-yloxy) carbonyl]amino]-propyl]amino]-3-phenylpropyl]sulfinyl]acetid acid;

[R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]-propyl]amino]-3-phenylpropyl]sulfonyl]acetic acid;

[R-(R*,S*)]-[[2-[[3-(1H-indol-3-yl)-2-methyl-1-oxo-2-[[(tricyclo[3.3.1.1$^{3,7}$]dec-2-yloxy) carbonyl]amino]-propyl]amino]-3-phenylpropyl]sulfinyl]acetic acid, ethyl ester;

[R-(R*,S*)]-[[2-[[3-(1H-indol-3-yl)-2-methyl-1-oxo-2-[[(tricyclo[3.3.1.1$^{3,7}$[dec-2-yloxy)]carbonyl]amino]-propyl]amino]-3-phenylpropyl]sulfonyl]acetic acid;

[R-[R*,R*-(E)]]-4-[[2-[[3-(1H-indol-3-yl)-2-methyl-1-oxo-2-[[(tricyclo[3.3.1.1$^{3,7}$]dec-2-yloxy)carbonyl]amino]-propyl]amino]-1-phenylethyl]amino]-4-oxo-2-butenoic acid;

[R-(R*,S*)]-[[2-[[2-[3-(1H-indol-3-yl)-2-methyl-1-oxo-2-[[(tricyclo[3.3.1.1$^{3,7}$]dec-2-yloxy)carbonyl]amino]-propyl]amino]-3-phenylpropyl]thio]acetic acid;

[1S-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid, methyl ester, (bicyclo system is 1S-endo);

[1S-[1α,2β[S*[S*(E)]],4α]]-4-[[2-[[3-(1H-indol-3-yl)-2-methyl-1-oxo-2-[[[(1,7,7-trimethylbicyclo-[2.2.1]hept-2-yl)oxy]carbonyl]amino]propyl]amino]-1-phenylethyl]amino]-4-oxo-2-butenoic acid (bicyclo system is 1S-endo);

[R-(R*,R*)]-3-[[2-[[3-(1H-indol-3-yl)-2-methyl-1-oxo-2-[[(tricyclo[3.3.1.1$^{3,7}$]dec-2-yloxy) carbonyl]amino]-propyl]amino]-1-phenylethyl]amino]-3-oxopropanoic acid;

[R-(R*,S*)]-3-(1H-indol-3-ylmethyl)-3-methyl-4,10-dioxo-6-(phenylmethyl)-11-oxo-8-thia-2,5-diazatridecanoic acid, tricyclo[3.3.1.1$^{3,7}$ ]dec-2-yl or ester;

[R-(R*,S*)]-β-[[3-(1H-indol-3-yl)-2-methyl-1-oxo-2-[[(tricyclo[3.3.1.1$^{3,7}$]dec-2-yloxy)-carbonyl]amino]-propyl]amino]benzenebutanoic acid;

[R-(R*,S*)]-β-[[3-(1H-indol-3-yl)-2-methyl-1-oxo-2-[[(tricyclo[3.3.1.1$^{3,7}$]dec-2-yloxy)carbonyl]amino]-propyl]amino]-4-iodo-benzenebutanoic acid, where the iodo group may be I-125 or I-127;

[R-(R*,S*)]—N-[3-[[3-(1H-indol-3-yl)-2-methyl-1-oxo-2-[[(tricyclo[3.3.1.1$^{3,7}$]dec-2-yloxy)carbonyl]-amino]-propyl]amino]-4-phenylbutyl]glycine; and

[R-[R*,S*-(E)]]-4-[[2-[[3-(1H-indol-3-yl)-2-methyl-2-[[(bicyclo [3.3.1]non-9-yloxy) carbonyl]amino]-1-oxopropyl]amino]-3-phenylpropyl]amino]-4-oxo-2-butenoic acid.

A most preferred compound for treating panic disorder symptoms is 2-[[3-(1H-indol-3-yl)-2-methyl-1-oxo-2-[[(tricyclo[3.3.1.1$^{3,7}$]dec-2-yloxy)carbonyl]amino]-propyl]amino]-1-phenylethyl butanedioate.

DETAILED DESCRIPTION

The compounds useful in the present invention are formed by the condensation of two modified amino acids and are therefore no peptides. Rather they are "dipeptoids", synthetic peptide-related compounds differing from natural dipeptides in that the substituent group $R^2$ is not hydrogen.

The compounds of the present invention are represented by the formula

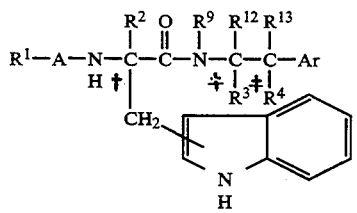 I or a pharmaceutically acceptable salt thereof wherein:
$R^1$ is a cyclo- or polycycloalkyl hydrocarbon of from three to twelve carbon atoms with from zero to four substituents, each independently selected from the group consisting of: a straight or branched alkyl of from one to six carbon atoms, halogen, CN, OR*, SR*, $CO_2R^*$, $CF_3$, $NR^5R^6$, or $(CH_2)_nOR^5$
wherein
R* is hydrogen, straight or branched alkyl of from one to six carbon atoms, $R^5$ and $R^6$ are each independently hydrogen or alkyl of from one to six carbon atoms; and
n is an integer from zero to six;
A is $(CH_2)_nCO—$, $—SO_2—$, $—S(=O)—$, $—NH-CO—$,

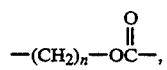

—SCO—, $O—(CH_2)_nCO—$ or —HC—CHCO—
wherein n is an integer from zero to six;
$R_2$ is a straight or branched alkyl of from one to six carbon atoms, $—HC=CH_2$, $—C≡CH$, $—CH_2—CH=CH_2$, $—CH_2C≡CH$, $—(CH_2)_nAr$, $—(CH_2)_nOR^*$, $—(CH_2)_nOAr$, $—(CH_2)_nCO_2R^*$, $—(CH_2)_nNR^5R^6$
wherein
n, R' $R^5$ and $R^6$ are as defined above and Ar is as defined below;
$R^3$ and $R^4$ are each independently selected from hydrogen, $R^2$ and $—(CH_2)_n—B—D$,
wherein
n' is an integer of from zero to three;
B is a bond —OCO(CH$_2$)$_n$—,
—O(CH$_2$)$_n$—,
—SO$_2$NH(CH$_2$)$_n$—,
—NHSO$_2$(CH$_2$)$_n$,
—NOCO(CH$_2$)$_n$—,
CONH(CH$_2$)$_n$—,
NHCOCH=CH—,
—COO(CH$_2$)$_n$—,
—CO(CH$_2$)$_n$—,
—S—(CH$_2$)$_n$—,
—SO(CH$_2$)$_n$—,
—SO$_2$(CH$_2$)$_n$—,

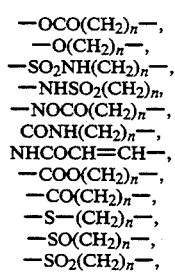

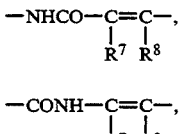

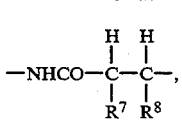

-continued

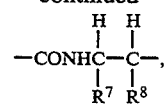

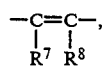

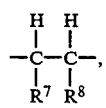

wherein $R^7$ and $R^8$ are independently selected from hydrogen and $R^2$ or together form a ring $(CH_2)_m$ wherein m is an integer of from 1 to 5 and n is as defined above;
D is
—COOR',
'CH$_2$OR*,
—CHR$^2$OR*,
—CH$_2$SR*,
—CR$^2$SR*,
—CONR$^5$R$^6$,
—CN,
—NR$^5$R$^6$,
—OH,
—H, and acid replacements such as tetrazole,
and

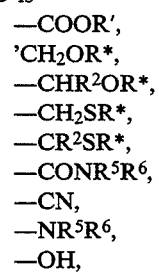

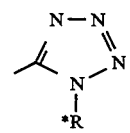

1,2,4 oxadiazole

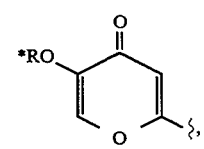 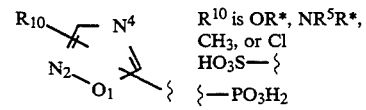

$R^{10}$ is OR*, $NR^5R^*$, $CH_3$, or Cl
$HO_3S—\}$
$\}—PO_3H_2$

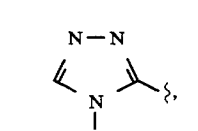 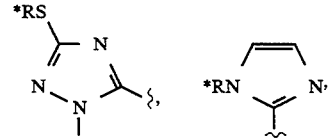

$R^{11}$ is CN, $CO_2H$, or $CF_3$,

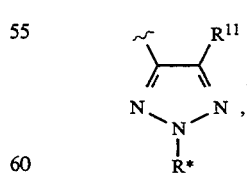

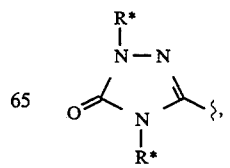

$PhSO_2NHCO—\}$, $CF_3CONHCO—\}$,
$CF_3SO_2NHCO—\}$, $H_2NSO_2—\}$,

-continued

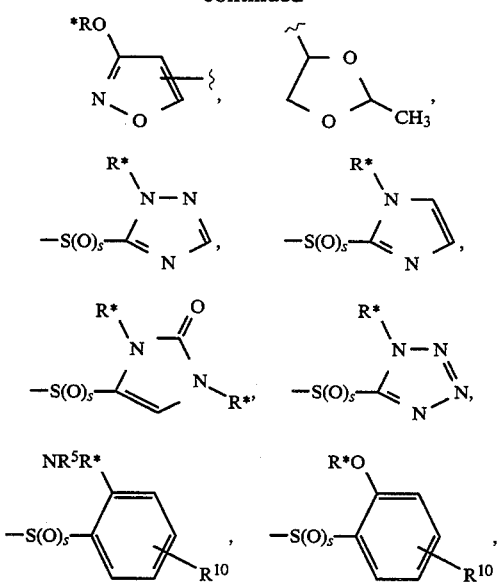

s is an integer of from 0 to 2
wherein R*, $R^2$, $R^5$, $R^6$ and $R^{10}$ are as defined above; $R^9$ is H, or a straight or branched alkyl of from one to six carbon atoms, —$(CH_2)_nCO_2R*$, $(CH_2)_nOAr'$, $(CH_2)_nAr'$, $(CH_2)_nNRSR^6$, wherein n R*, $R^5$ and $R^6$ are as defined above or taken from $R^3$ and Ar' is taken from Ar as defined below;

$R^{12}$ and $R^{13}$ can each be independently hydrogen (in which case the carbon atom to which it is attached is a chiral center) or can each be taken with $R^3$ and $R^4$ respectively to form a moiety doubly bonded to the carbon atom (in which case the carbon atom is not chiral) and Ar is a mono- or polycyclic unsubstituted or substituted carbo- or heterocyclic aromatic or hydroaromatic moiety.

Preferred Ar is

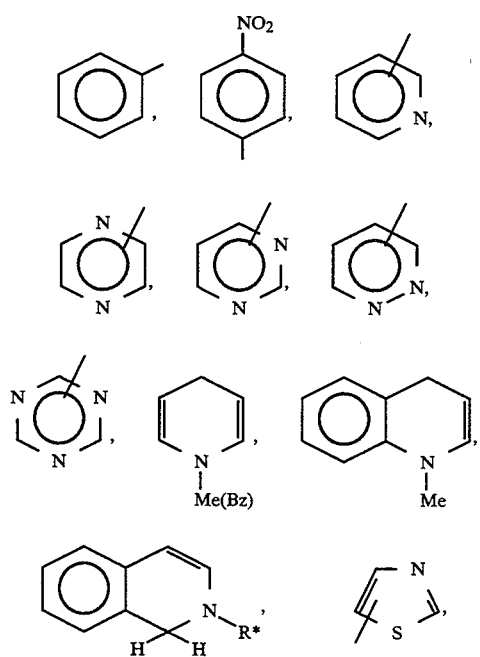

-continued

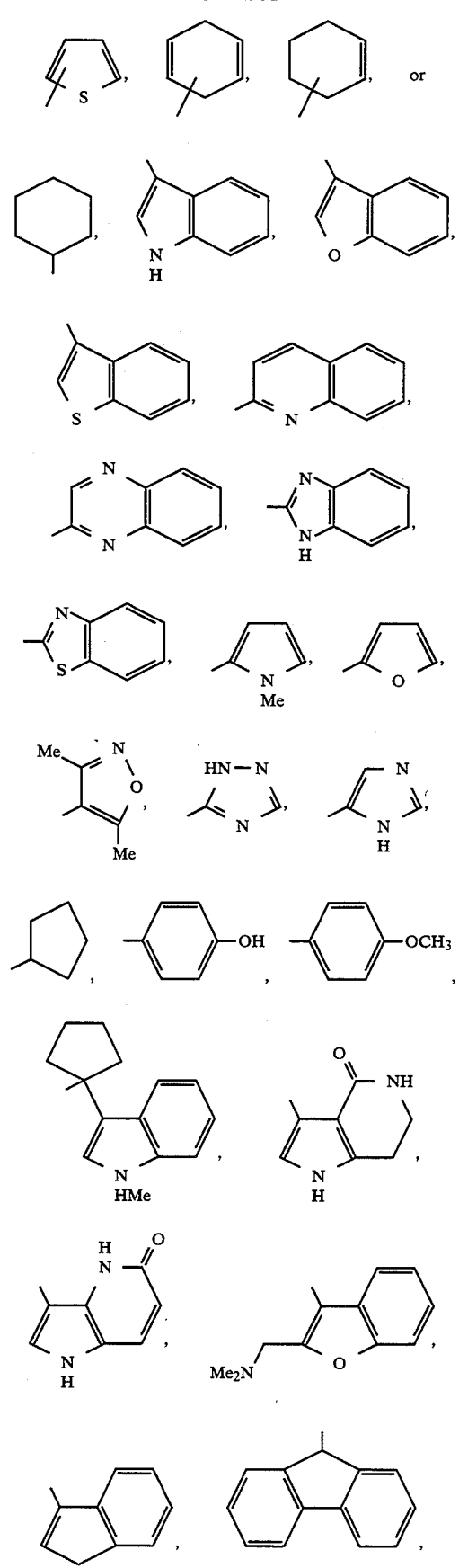

-continued
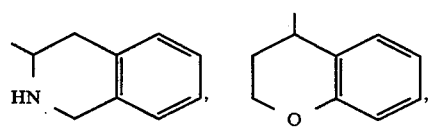
—CHPh₂, 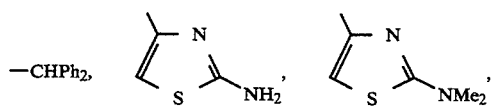
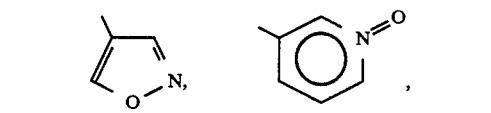
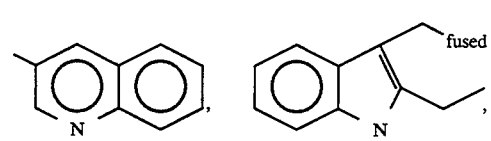
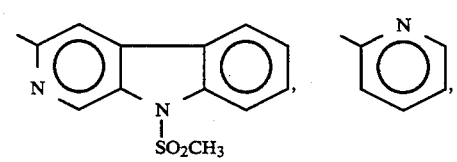
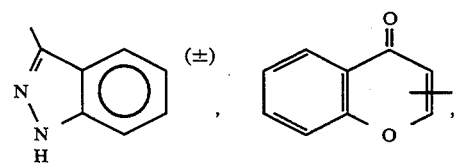
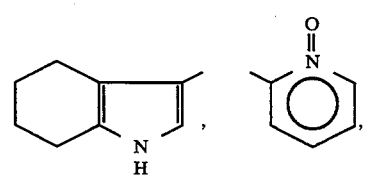
3-pyridyl,
4-pyridyl,
4-pyridyl N-oxide, 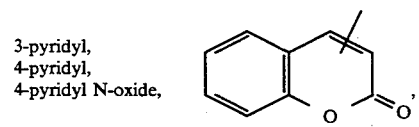
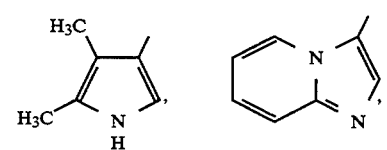
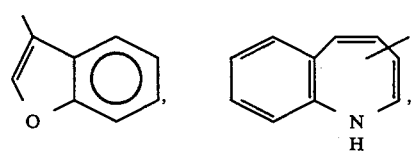
-continued
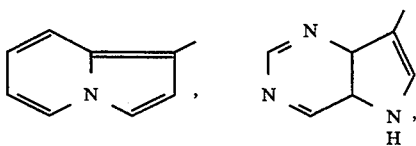
1-naphthyl,
2-naphthyl, 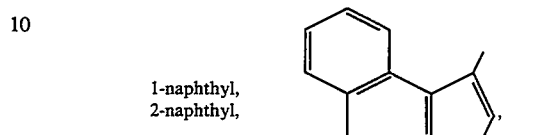
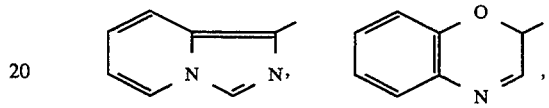
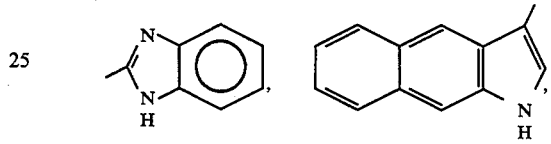
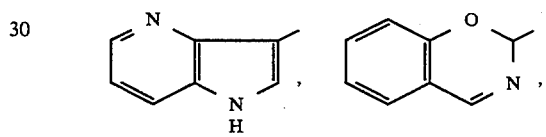
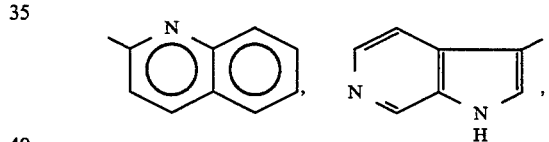
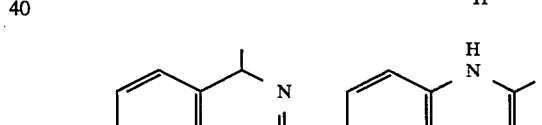
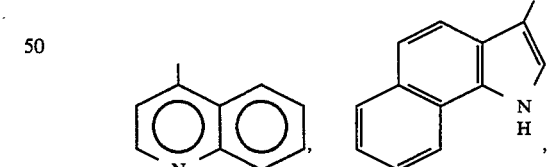
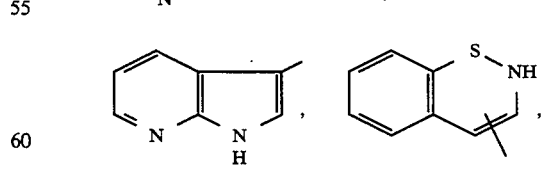
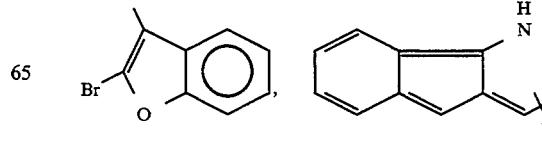

-continued

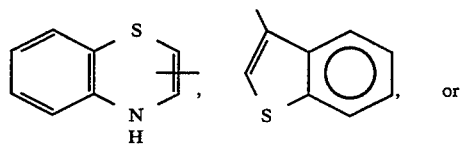

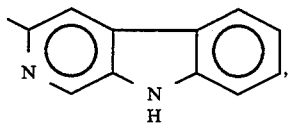

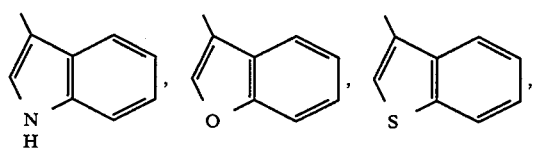

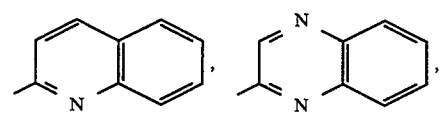

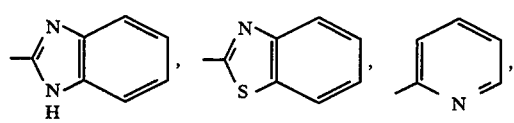

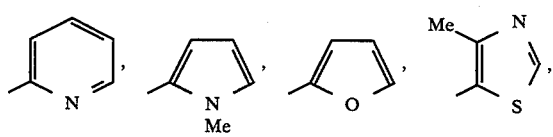

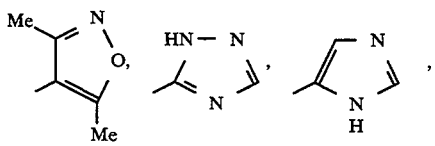

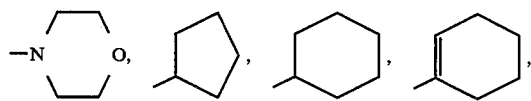

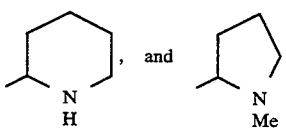

Still more preferred Ar is 2- or 3-thienyl, 2- or 3-furanyl, 2-, 3- or 4-pyridinyl or an unsubstituted or substituted benzene ring

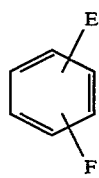

wherein E and F are each independently hydrogen, fluorine, chlorine, bromine, iodine, methyl, methoxy, trifluoromethyl, nitro, hydroxy, $NH_2$, $OCF_3$, and $R^3$ as defined above. Preferred definition for $R^3$ is $NHCOCH_2CH_2CO_2H$ or $CH_2CH_2CO_2H$.

The indole portion of formula I can be mono or disubstituted by halogen; lower alkyl; $CF_3$; lower alkoxy; benzyloxy; hydroxy;

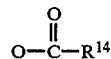

wherein $R^{14}$ is lower alkyl or phenyl; $—NO_2$; $NR_1{}^{15}R_2{}^{16}$ where $R_1{}^{15}$ and $R_2{}^{16}$ are each independently hydrogen or lower alkyl;

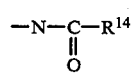

wherein $R^{14}$ is as defined above.

Preferred substituents are 5-fluoro, 5-chloro; 5-hydroxy; 5-methyl; 5-methoxy; 5-benzyloxy; 5—$CF_3$, —$NO_2$; and 5-$NH_2$.

The indole is numbered

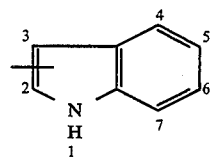

for purposes of the above substituents.

Further, the indole can be substituted on the nitrogen by -[(4-methylphenyl)sulfonyl] or by a methyl group.

Preferred cycloalkyl or polycycloalkyl substituents have from six to ten carbon atoms.

Preferred compounds of the instant invention are those wherein cycloalkyl is a substituted or unsubstituted

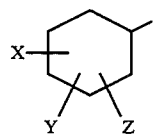

and wherein polycycloalkyl is selected from

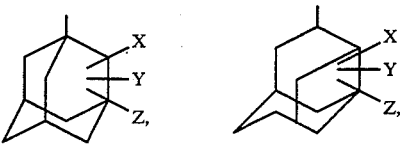

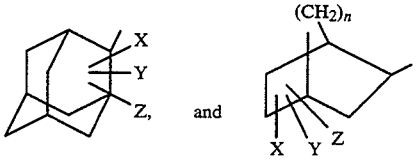

wherein W, X, Y, and S are each independently hydrogen, a straight or branched alkyl of from one to six carbon atoms, $CF_3$, $NR^5R^6$, $—(CH_2)_nCO_2R^*$, or CN, F, Cl, St, $OR^*$, $SR^*$, wherein R' is hydrogen or a straight or branched alkyl of from one to six carbon atoms and $R^5$ and $R^6$ are as defined above and n is an integer of from 1 to 3.

Other preferred compounds of the instant invention are those wherein $R^1$ is 2-adamantyl or 1-(S)-2-endobornyl;
A is —NHCO—, —OCO—, —$SO_2$—, —S(=O)- or —$CH_2CO$—;
$R^2$ is —$CH_3$, —$CH_2CO_2CH_3$ or —$CH_2C≡CH$;
$R^3$ is —$(CH_2)_n$,—B—D or H;
$R^4$ is —$(CH_2)_n$,—B—D or H; and
$R^9$ is hydrogen or methyl.

More preferred compounds of the instant invention are those wherein

R1 is 2-adamantyl, 1-(S)-2-endobornyl, or 2-methylcyclohexyl;

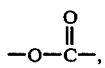

A is —O—C—,
$R_2$ is —$CH_3$;
$R^3$ is H, $CH_2OH$, —$CH_2OCOCH_2CH_2CO_2H$, —$CH_2OCOCH=CHCO_2H$ or —$CH_2NHCOCH_2CH_2CO_2H$, or —$CH_2NHCOCH=CHCO_2H$ and
$R^4$ is H, —$CH_2SCH_2CO_2H$, —$CH_2SCH_2CH_2CO_2H$, —$NHCOCH=CHCO_2H$, —$NHCOCH_2CH_2CO_2H$ ([D] configuration or —$NHCOCH=CHCO_2H$ ((D] configuration).

The D and the L configurations are possible at the chiral centers d are included in the scope of the invention:

1. Preferred is when $R^2$ —$CH_3$[D]configuration;
2. Preferred is when $R^3$ is —$CH_2OCOCH_2CH_2CO_2H$ or $CH_2CO_2H$ or —$CH_2NHCOCH_2CH_2CO_2H$ with the ID] configuration at the Trp α-carbon atom and the [L] configuration at the Phe-α-carbon atom; d
3. Preferred is when $R^4$ is —$NHCOCH_2CH_2CO_2H$ [D] configuration or COCH=$CHCO_2H$[D] configuration with the ID) configuration at the Trp α-carbon atom.

Most preferred compounds of the instt invention are:
1. [1S-[1α,2β[S*[S*(E)]],4α]]-4-[[2-[[3-(1H-indol-3-yl)-2-methyl-1-oxo-2-[[[(1,7,7-trimethylbicyclo-[2.2.1]hept-2-yl)oxy]carbonyl]amino]propyl]amino]-1-phenylethyl]amino]-4-oxo-2-butenoic acid,
2. [1S-[1α,2β[S*(S*)],4α]]-4-[[2-[[3-(1H-indol-3-yl)-2-methyl-1-oxo-2-[[[(1,7,7-trimethylbicyclo-[2.2.1]hept-2-yl)oxy]carbonyl]amino]propyl]methylamino]-1-phenylethyl]amino]-4-oxobutanoic acid,
3. [1S-[1α,2β[S*(S*)],4]]-4-[[2-[[3-(1H-indol-3-yl)-2-methyl-1-oxo-2-[[[(1,7,7-trimethylbicyclo-2.2.1]hept-2-yl)amino]carbonyl]amino]propyl]ino]-1-phenylethyl]amino]-4-oxobutanoic acid,
4. [R-(R*,R*)]-4-[[2-[[3-(1H-indol-3-yl)-2-methyl-1-oxo-2-[(tricyclo[3.3.1.1$^{3,7}$]dec-2-ylsulfonyl)amino]propyl]amino]-1-phenylethyl]amino]-4-oxobutanoic acid,
5. JR-(R*,S*)]-4-[[2-[[3-(1H-indol-3-yl)-2-methyl-1-oxo-2-[(tricyclo[3.3.1.1$^{3,7}$]dec-2-ylsulfonyl)amino]propyl]amino]-3-phenylpropyl]amino]-4-oxobutanoic acid,
6. [1R-[1α[R*(S*)],2β]]and [1S-[1α[S*(R*)],2β]]-4-[2-[[2-[[[(2-fluorocyclohexyl)oxy]carbonyl]amino]-3-(1H-indol-3-yl)-2-methyl-1-oxopropyl]amino]-3-phenylpropyl]amino]-4-oxobutanoic acid,
7. [1R-[1α[R*(S*)],2β]]and [1S-[1α[S*(R*)],2β]]-4-[2-[[2-[[[(2-fluorocyclohexyl)oxy]carbonyl]amino]-3-(1H-indol -3-yl)-2-methyl-1-oxopropyl]methylamino]-3-phenylpropyl]amino]-4-oxobutanoic acid,
8. [1R-[1α[R*(S*)], 2β]] and [1S-[1α[S*(R*)],2β]]-4-[2-[[3-(1H-indol-3-yl)-2-methyl-1-oxo-2-[[[[2-(trifluoromethyl)cyclohexyl]oxy]carbonyl]amino]propyl]amino]-3-phenylpropyl]amino]-4-oxobutanoic acid,
9. [1R-[1αR*(S*)],2β]] and [1S-[1α[S*(R*)],2β]]-4-[[2-[[3-(1H-indol-3-yl)-2-methyl-1-oxo-2-[[[[2-(trifluoromethyl)cyclohexyl]oxy]carbonyl]amino]propyl]methylamino]-3-phenylpropyl]amino]-4-oxobutanoic acid,
10. [R-(R*,S*)]-4-[[2-[[3-(1H-indol-3-yl)-2-methyl-1-oxo-2-[[(tricyclo[3.3.1.1$^{3,7}$]dec-2-yloxy)carbonyl]amino]propyl]methylamino]-3-phenylpropyl]amino]-4-oxobutanoic acid,
11. [1S-[1α,2β[S*(R*)],4α]]-[1-(1H-indol-3-ylmethyl)-1-methyl-2-oxo-2-[[2-[[1-oxo-3-(1H-tetrazol-5-yl)propyl]amino]-1-(phenylmethyl)ethyl]amino]ethyl]-carbamic acid, 1,7,7-trimethylbicyclo[2.2.1]hept-2-yl ester,
12. [1S-[1α,2β[S*(R*)],4α]]-[1-(1H-indol-3-ylmethyl)-1-methyl-2-oxo-2-[[2-[[1-oxo-3-(1H-tetrazol-5-yl)-propyl]amino]-2-phenylethyl]amino]ethyl]carbamic acid, 1,7,7-trimethyl-bicyclo [2.2.1]hept-2-yl ester,
13. N-[2-methyl-N-[(tricyclo[3.3.1.1$^{3,7}$]dec-2-yloxy)carbonyl]-D-tryptophyl]-L-phenylalanylglycine,
14. N-[2-methyl-N-[(tricyclo[3.3.1.1$^{3,7}$]dec-2-yloxy)-carbonyl]-D-tryptophyl]-L-phenylalanyl-β-alanine and
15. (R)-tricyclo[3.3.1.1$^{3,7}$]dec-2-yl[1-(1H-indol-3-ylmethyl)-1-methyl-2-[methyl(2-phenylethyl)amino]-2-oxoethylcarbamate.

In addition most especially preferred compounds of the instant invention are:
16. (±)-Trans-2-chlorocyclohexyl[1-(1H-indol-3-ylmethyl)-1-methyl-2-oxo-2-[(2-phenylethyl)amino]ethyl]carbamate,
17. 2-chlorocyclohexyl[2-[[1-(hydroxymethyl)-2-phenylethyl]amino]-1-(1H-indol-3-ylmethyl)-1-methyl-2-oxoethyl]carbamate,
18. 2-[[2-[[[(2-chlorocyclohexyl)oxy]carbonyl]amino]-3-(1H-indol-3-yl)-2-methyl-1-oxopropyl]amino]-3-phenylpropyl butanedioate,
19. 2-[[2-[[[(2-methylcyclohexyl)oxy]carbonyl]amino]-3-(1H-indol-3-yl)-2-methyl-1-oxopropyl]amino]-3-phenylpropyl butanedioate,
20. (±)-tricyclo[3.3.1.1$^{3,7}$]dec-2-yl[1-(1H-indol-3-ylmethyl)-1-methyl-2-oxo-2-[(2-phenylethyl)amino]ethylcarbamate,
21. tricyclo[3.3.1.1$^{3,7}$]dec-2-yl[2-[[1-(hydroxymethyl)-2-phenylethyl]amino]-1-(1H-indol-3-yl-methyl)-1-methyl-2-oxoethyl]carbamate,
22. 2-[[3-(1H-indol-3-yl)-2-methyl-1-oxo-2-[[(tricyclo-[3.3.1.1$^{3,7}$]dec-2-yloxy) carbonyl]amino]propyl]amino]-3-phenylpropyl butanedioate,
23. 2-[[3-(1H-indol-3-yl)-2-methyl-1-oxo-2-[[(tricyclo[3.3.1.1$^{3,7}$]dec-2-yloxy) carbonyl]amino]propyl]amino]-1-phenylethyl butanedioate,
24.-[R-(R*,R*)]-4-[[2-[[3-(1H-indol-3-yl)-2-methyl-1-oxo-2-[[(tricyclo[3.3.1.1$^{3,7}$]dec-2-yloxy) carbonyl]amino]propyl]amino]-1-phenylethyl]amino]-4-oxobutanoic acid, 25. [1S-[1α,2β[S*(S*)],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxobutanoic acid, 26. [R-[R*,S*-(E)]]-4-[[2-[[3-(1H-indol-3-yl)-2-methyl-1-oxo-2-[[tricyclo[3.3.1.1$^{3,7}$]dec-2-yloxy)carbonyl]amino]propyl]amino]-3-phenylpropyl]amino]-4-oxo-2-butenoic acid, 27. [R-(R*,S*)]-4-[[2-[[3-(1H-indol-3-yl)-2-methyl-1-oxo-2-[[(tricyclo[3.3.1.1$^{3,7}$]dec-2-yloxy) carbonyl]amino]propyl]amino]-3-phenylpropyl]amino]-4-oxobutanoic acid, 28. (R)-tricyclo[3.3.1.1$^{3,7}$]dec-2-yl[1-(1H-indol-3-ylmethyl)-1-methyl-2-[methyl(2-phenylethyl)amino]-2-oxoethylcarbamate, 29. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfinyl]acetic acid, ethyl ester, 30. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfonyl]acetic acid, ethyl ester, 31. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sul finyl]acetic acid, 32. JR-[R*,R*-(E)]]-4-[[2-[[3-(1H-indol-3-yl)-2-methyl-1-oxo-2-[[(tricyclo[3.3.1.1$^{3,7}$]dec-2-yloxy)]carbonyl]amino]propyl]amino]-1-phenylethyl]amino]-4-oxo-2-butenoic acid, 33. [R-(R*,S*)]-[[2-[[2-[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]thio]acetic acid, 34. [1S-[1,2[S*[S*(E)]],4i]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid, methyl ester, (Bicyclo system is 1S-endo), 35. [1S-[1α,2β[S*[S*(E)]],4]]-4-[[2-[[3-(1H-indol-3-yl)-2-methyl-1-oxo-2-[[[(1,7,7-trimethylbicyclo[2.2.1]hept-2-yl)oxy ]carbonyl]amino]propyl]amino]-1-phenylethyl]amino]-4-oxo-2-butenoic acid, (Bicyclo system is 1S-endo) , 36. [R-(R*,R*)]-3-[[2-[[3-(1H-indol-3-yl)-2-methyl-1-oxo-2-[[(tricyclo[3.3.1.1$^{3,7}$]dec-2-yloxy)]carbonyl]amino]propyl]amino]-1-phenylethyl]amino]-3-oxopropanoic acid, 37. [R-(R*,S*)]-3-(1H-indol-3-ylmethyl)-3-methyl-4,10-dioxo-6-(phenylmethyl)-11-oxo-8-thia-2,5diazatridecanoic acid, tricyclo[3.3.1.1$^{3,7}$]dec-2-yl or ester, 38. [R-(R*,S*)]-β-[[3-(1H-indol-3-yl)-2-methyl-1-oxo-2-[[(tricyclo[3.3.1.1$^{3,7}$]dec-2-yloxy)]carbonyl]amino]propyl]amino]benzenebutanoic acid, 39. [R-(R*,S*)]-N-J3-[[3-[[3-(1H-indol-3-yl)-2-methyl-1-oxo-2-[[(tricyclo[3.3.1.1$^{3,7}$]dec-2-yloxy)]carbonyl]amino]propyl]amino]-4-phenylbutyl]glycine, 40. [R-[R*,S*-(E)]]-4-[[2-[[3-(1H-indol-3-yl)-2-methyl-2-[[(bicyclo [3.3.1]non-9-yloxy) carbonyl]amino]-1-oxopropyl]-amino]-3-phenylpropyl]amino]-4-oxo-2-butenoic acid, 41. mono [R-(R*,R*)]-2-[[3-(1H-indol-3-yl)-2-methyl-1-oxo-2-[[(tricyclo[3.3.1.1$^{3,7}$]dec-2-yloxy)carbonyl]amino]-1-phenylethyl butanedioate, 42. 3-[[3-[[3-(1H-indol-3-yl)-2-methyl-1-oxo-2-[[(tricyclo-[3.3.1.1$^{3,7}$]dec-2-yloxy)]carbonyl]amino]propyl]amino]-1-oxo-2-phenylpropylamino]propanoic acid (TRP is R, other center is RS), 43. [1R-[I[R*(S*)],β2]]-4-[[2-[[3-(1H-indol-3-yl)-2-methyl-2-[[[(2-methyl-1-cyclohexyl)oxy]carbonyl]amino]-1-oxopropyl]-amino]-3-phenylpropyl]amino]-4-oxo-2-butenoic acid, (−)-Isomer, 44. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]-amino]-3-phenylpropyl]amino]-4-oxobutanoic acid, (−)-Isomer, 45. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]-amino]-1-phenylethyl]amino]-4-oxo-2-butenoic acid, (−)-Isomer, 46. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]-amino]-1-phenylethyl]amino]-4-oxobutanoic acid, (−)-Isomer, 47. 2-methylcyclohexyl-[1R-[1α[R*(S*)]],2β]-[2-[[1-(hydroxymethyl)-2-phenylethyl]amino]-1-(1H-indol -3-ylmethyl)-1-methyl-2-oxoethyl]carbamate, 48. [R-[R*,S*-(E,E)]]-6-[[3-(1H-indol-3-yl)-2-methyl-1-oxo-2-[[(tricyclo-[3-3-1.1$^{3,7}$]dec-2-yloxy)carbonyl]amino]propyl]-amino]-7-phenyl-2,4-heptadienoic acid, 49. [R-(R*,R*)]-[2-[[2-[[1,4-dioxo-4-(1H-tetrazol-5-ylamino)-butyl]amino]-2-phenylethyl]amino]-1-(1H-indol-3-ylmethyl)-1-methyl-2-oxoethyl]carbamic acid, 50. tricyclo-[3.3.1.1$^{3,7}$]dec-2-yl-[S-[R*,S*-(E)]]-12-(1H-indol-3-ylmethyl)-12-methyl-3,11-dioxo-9-(phenylmethyl)-2-oxa-7,10,13-triazatetradec-4-en-14-oate, 51. [R-(R*,S*)]-3-[[2-[[3-(1H-indol-3-yl)-2-methyl-1-oxo-2-[[(tricyclo-[3.3.1.1$^{3,7}$]dec-2-yloxy)carbonyl]amino]propyl]-amino]-3-phenylpropyl]amino]-3-oxopropanoic acid, 52. ethyl[R-(R*,S*)]-[[2-[[2-[3-(1H-indol-3-yl)-2-methyl-1-oxo-2-[[(tricyclo[3.3.1.1$^{3,7}$]dec-2-yloxy)carbonyl]amino]-propyl]amino]-3-phenylpropyl]thio]acetate, 53. [R-(R*,S*)]-β-[[3-(1H-indol-3-yl)-2-methyl-1-oxo-2-[[tricyclo[3.3.1.1$^{3,7}$]dec-2-yloxy) carbonyl]amino]propyl]amino]-4-iodo-benzenebutanoic acid, 54. [R-(R*,R*)]-[2-[[3-(1H-indol-3-yl)-2-methyl-1-oxo-2-[[(1(tricyclo[[(3.3.1.1$^{3,7}$]dec-2-yloxy)-carbonyl]amino]-propyl]amino]-1-phenylethoxy ]acetic acid, 55. [[3-[[3-(1H-indol-3-yl)-2-methyl-1-oxo-2-[[tricyclo(3.3.1.1$^{3,7}$]dec-2-yloxy) carbonyl]amino]propyl]amino]-1-oxo-2-phenylpropyl]amino]acetic acid (TRP center is R, other center is RS) , 56. (R)-[[[2-[[3-(1H-indol-3-yl)-1-oxo-2-methyl-2-[[(tricyclo[3.3.1.1$^{3,7}$]dec-2-yloxy) carbonyl]amino]propyl]amino]-1-phenylethylidene]amino]oxy]acetic acid, 57. [R-(R*,S*)]-β-[[3-(1H-indol-3-yl)-2-methyl-1-oxo-2-[[(tricyclo[3.3.1.1$^{3,7}$]dec-2-yloxy)carbonyl]amino]-propyl]-amino]benzenebutanoic acid, 58. [R-(R*,S*)]—N-[3-[[3-(1H-indol-3-yl)-2-methyl-1-oxo-2-[[(tricyclo-[3.3.1.1$^{3,7}$]dec-2-yloxy)carbonyl]-propyl]amino]-4-phenylbutyl]glycine, 59. 2-[[[2-[[3-(1H-indol-3-yl)-2-methyl-1-oxo-2-[[(tricyclo-[3.3.1.1$^{3,7}$]dec-2-yloxy) carbonyl]amino]-propyl]amino]-1-phenylethyl]amino]carbonyl]cyclopropanecarboxylic acid (cyclopropane ring is trans-(±) other centers are R), 60. carbamic acid, [1-(1H-indol-3-ylmethyl)-1-methyl-2-oxo-2-[[2-[[1-oxo-3-(1H-tetrazol-5-yl) propyl]amino]-2-phenylethyl]-amino]ethyl]-, tricyclo[3.3.1.1$^{3,7}$]dec-2-yl ester, [R, (R*,S*]-, 61. benzeneheptanoic acid, α-[[3-(1H-indol-3-yl)-2-methyl-1-oxo-2-[[(tricyclo[3.3.1.1$^{3,7}$]dec-2-yloxy)carbonyl]amino]-propyl]amino]-, [R-(R*,S*)]-, 62. methyl-(±)-β-[[(2-phenylethyl)amino]carbonyl]-1β-[[(tricyclo[3.3.1.1³,⁷]dec-2-yloxy) carbonyl]amino]-1H-indole-3-butanoate, 63. [R-(R*,S*)]-4-[[2-(1H-indol-3-yl)-2-methyl-1-oxo-2-[[tricyclo[3.3.1.1³,⁷]dec-2-yloxylcarbonyl]amino]-propyl]-amino]-3-phenylpropyl]amino]-4-oxo-2-butenoic acid, 64. bicyclo[2.2.1]heptane-2-acetic acid, 3-[[[[2-[[1-(hydroxymethyl)-2-phenylethyl]amino]-1-(1H-indo 1-3-ylmethyl)-1-methyl-2-oxoethyl]amino]carbonyl]oxy]-4,7,7-trimethyl-, [1R-[1α,2β,3α[R*(S*)], 4α]]-, 65. butanoic acid, 4-[[2-[[3-(1H-indol-3-yl)-2-methyl-2-[[[(2-methyl-1-cyclohexyl)oxy]carbonyl]amino]-1-oxopropyl]-amino]-1-phenylethyl]amino]-4-oxo-1R-[1[R*(R*)]2]]-((−)-isomer) , 66. 2-butenoic acid, 4-[[2-[[3-(1H-indol-3-yl)-2-methyl-2-[[[(2-methyl-1-cyclohexyl)oxy]carbonyl]amino]-1-oxopropyl]-amino]-1-pheny 1 ethyl]amino]-4-oxo-1R-[1[R*(R*)],2]]-((−)-isomer) , 67. butanoic acid, 4-[[2-[[3-(1H-indol-3-yl)-2-methyl-2-[[[(2-methyl-1-cyclohexyl)oxy]carbonyl]amino]-1-oxopropyl]-amino]-3-phenylpropyl]amino]-4-oxo-[1R-[1α[R*(S*)],2β]]-((−)-isomer), and 68. 2-butenoic acid, 4-[[2-[[3-) 1H-indol-3-yl)-2-methyl-2-[[[(2-methyl-1-cyclohexyl)oxy]carbonyl]amino]-1-oxopropyl]-amino]-3-phenylpropyl]amino]-4-oxo-[1R[-1α[R*(S*)],2β]]-((−)-isomer).

Additionally preferred are the compounds:

69. [[3-[[3-(1H-indol-3-yl)-2-methyl-1-oxo-2-[[tricyclo[3.3.1.1³,⁷]dec-2-yloxy)carbonyl]amino]propyl]amino]-1-oxo-2-phenylpropyl]amino]acetic acid (TRP center is R, other center is RS), 70. [R-(R*,R*)]-2-[[2-[[3-(1H-indol-3-yl)-2-methyl-1-oxo-2-[[(tricyclo[3.3.1.1³,⁷]dec-2-yloxy) carbonyl]amino]propyl]amino]-1phenylethoxy]acetic acid, 71. [1R-[1α,2β[R*(R*)]]]-2-[[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino]carbonyl]cyclopropane carboxylic acid, 72. [1S-[1α,2β[S*(S*)]]]-2-[[[2-[[3-(1H-indol-3-yl)-2-methyl-1-oxo-2-[[(tricyclo[3.3.1.1³,⁷]dec-2-yloxy)-carbonyl]amino]propyl]amino]-1-phenylethyl]amino]-carbonyl]cyclopropane carboxylic acid, 73. [R-R*,R*)]-3-[2-[[3-(1H-indol-3-yl)-2-methyl-1-oxo-2-[[(tricyclo[3.3.1.1³,⁷]dec-2-yloxy)carbonyl]amino]propyl]amino]-1-phenylethoxy]propanoic acid, 74. [R-(R*,R*)]-mono 2-[3-(1H-indol-3-yl)-2-methyl-1-oxo-2-[[(tricyclo[3.3.1.1³,⁷]dec-2-yloxy) carbonyl]amino]-1-phenylethyl butanedioic acid, 75. 3-[[3-[[3-(1H-indol-3-yl)-2-methyl-1-oxo-2-[[(tricyclo[3.3.1.1³,⁷]dec-2-yloxy) carbonyl]amino]-propyl]amino]-1-oxo-2-phenylpropyl]amino]propanoic acid, (TRP is R, other center is RS), 76. [R-(R*,S*)]--[[3-(1H-indol-3-yl)-2-methyl-1-oxo-2-[[(tricyclo[3.3.1.1³,⁷]dec-2-yloxy) carbonyl]amino]propyl]amino]-4-iodobenzenebutanoic acid, 77. [1R-[1αR*(S*)],2β]]-4-[[2-[[3-(1H-indol-3-yl)-2-methyl-2-[[[(2-methyl-1-cyclohexyl)oxy]carbonyl-]amino]-1-oxopropyl]amino]-3-phenylpropyl]amino]-4-oxo-2-butenoic acid, ((−)-isomer) , 78. [1-([1α[R*(S)],(S)*2β]]-4-[[2-[[3-(1H-indol-3-yl)-2-methyl-2-[[[(2-methyl-1cyclohexyl)oxy ]carbonyl]-amino]-1-oxopropyl]amino]-3-phenylpropyl]amino]-4-oxobutanoic acid, ((−)-isomer), 79. [1R-[1α[R*(R*)],2β]]-4-[[2-[[3-(1H-indol-3-yl)-2-methyl-2-[[[(2-methyl-1-cyclohexyl)oxy ]carbonyl-]amino]-1-oxopropyl]amino]-1-phenylethyl]amino]-4-oxo-2-butenoic acid, ((−)-isomer), 80. 1R-[1α[R*(R*)],2β]]-4-[[2-[[3-(1H-indol-3-yl)-2-methyl-2-[[[(2-methyl-1-cyclohexyl)oxy]carbonyl-]amino]-1-oxopropyl]amino]-1-phenylethyl]amino]-4-oxobutanoic acid, ((−)-isomer), 81. [R-(R*,S*)]-1δ-[[3-(1H-indol-3-yl)-2-methyl-1-oxo-2-[[(tricyclo[3.3.1.1³,⁷]dec-2-yloxy) carbonyl-]amino]propyl]benzeneheptanoic acid, 82. 2-[[[2-[[3-(1M-indol-3-yl)-2-methyl-1-oxo-2-[[(tricyclo[3.3.1.1³,⁷]dec-2-yloxy) carbonyl]amino]-propyl]amino]-1-phenylethyl]amino]carbonyl]-cyclopropanecarboxylic acid (cyclopropyl ring is trans-(±), other centers are R), 83. 2-methylcyclohexyl[1R-[I[R*(S*)]],2]-[2-[[1-(hydroxymethyl)-2-phenylethyl]amino]-1-(1H-indol-3-ylmethyl)-1-methyl-2-oxoethyl]carbamate, ((−)-isomer, 84. [R-[R*,S*-(E,E)]]-6-[[3-(1H-indol-3-yl)-2-methyl-1-oxo-2-[[(tricyclo[3.3.1.1³,⁷ ]dec-2-yloxy) carbonyl-]amino]propyl]amino]-7-phenyl-2,4-heptadienoic acid, 85. tricyclo[3.3.1.1³,⁷]dec-2-yl[2-[[1-(hydroxymethyl)-2-hydroxy-2-phenylethyl]amino]-1-(1H-indol-3-ylmethyl)-1-methylethyl]carbamate, 86. tricyclo[3.3.1.1³,⁷]dec-2-yl[R-(R*,R*)]-[1-(1H-indol-3-ylmethyl)-1-methyl-2-oxo-2-[[2-[[1-oxo-3-(1H-tetrazol-5-yl) propyl]amino]-2-phenylethyl]amino]ethyl]carbamate, 87. [R-(R*,S*)]-2-[[2-[[3-(1H-indol-3-yl)-2-methyl-1-oxo-2-[[(tricyclo[3.3.1.1³,⁷]dec-2-yloxy) carbonyl]-amino]propyl]amino]-3-phenylpropyl]sulfinyl]acetic acid, 88. [R-(R*,S*)]-[[2-[[3-(1H-indol-3-yl)-2-methyl-1-oxo-2-[[(tricyclo[3.3.1.1³,⁷]dec-2-y.loxy)]ca=bonyl-]amino]propyl]amino]-3-phenylpropyl]sulfonyl]acetic acid, 89. Ethyl[R-(R*,S*)]-[[2-[[3-(1H-indol-3-yl)-2-methyl-1-oxo-2-[[(tri cycl o [3.3.1.1³,⁷ ]dec-2-yloxy)]carbonyl]amino]propyl]amino]-3-phenylpropyl]sulfonyl-]acetate, 90. 2-chlorocyclohexyl[2-[[1-(hydroxymethyl)-2-phenylethyl]amino]-1-(1H-indol -3-ylmethyl)-1-methyl-2-oxoethyl]carbamate, Isomer II, ring centers are trans, trp center is D, other center is S) ((−) or (+) form), 91. JR-[R*,R*(E)]]-4-[[2-[[3-(1M-indol-3-yl)-2- methyl-1-oxo-2-[[(tricyclo[3.3.1.1³,⁷]dec-2ylamino) carbonyl]amino]propyl]amino]-1phenylethyl ]amino]-4-oxo-2-butenoic acid, 92. [R-(R*,R*)]-4-[[2-[[3-(1H-indol-3-yl)-2-methyl-1-oxo-2-[[(tricyclo[3.3.1.1³,⁷]dec-2-yloxy) carbonyl-]amino]propyl]amino]-1-phenylethyl]amino]-4-oxobutanoic acid, 93. [R-(R*,S*)]-mono[2-[[3-(1H-indol-3-yl)-2-methyl-1-oxo-2-[[(tricyclo[3.3.1.1³,⁷]dec-2-yloxy) carbonyl-]amino]propyl]amino]-3-phenylpropyl]butanedioate, 94. tricyclo[3.3.1.1³,⁷]dec-2-yl[R-(R*,S*)-2-[[1-(hydroxymethyl)-2-phenylethyl]amino]-1-(1H-indol-3-ylmethyl)-1-methyl-2-oxoethyl]-carbamate, 95. [1S-[1α,2[S*[S*(E)]],4]]-4-[[2-[[3-(1H-indol-3-yl)-2-methyl-1-oxo-2-[[[(1,7,7-trimethylbicyclo[2.2.1 ]hept-2-yl)oxy ]carbonyl]amino]-propyl]amino]-1-phenylethyl]amino]-4-oxo-2-butenoic acid (bicyclo system is 1S-endo), 96. [1S-[1α,2[S*(S*)],4]]-4-[[2-[[3-(1H-indol-3-yl)-2-methyl-1-oxo-2-[[[(1,7,7-trimethylbicyclo-[2.2.1 ]hept-2-y 1 )oxy ]carbonyl]-aminopropyl]amino]-1-phenylethyl]amino]-4-oxo-2-butenoic acid (bicyclo system is 1S-endo), 97. [R-[R*,S*-(E)]]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxo-2-butenoic acid, 98. N-[2-methyl—N-[(tricyclo[3.3.1.1$^{3,7}$]dec-2-yloxy)carbonyl]-D-tryptophyl]-L-phenylalanylglycine, 99. [R-(R*,S*)]-4-[[2-[[3-(1H-indol-3-yl)-2-methyl-1-oxo-2-[[(tricyclo[3.3.1.1$^{3,7}$]dec-2-yloxy) carbonyl]amino]propyl]amino]-3-phenylpropyl]amino]-4-oxobutanoic acid, 100. [R-(R*,R*)]-2-[[2-[[1,4-dioxo-4-(1H-tetrazol-5-ylamino)butyl]amino]-2-phenylethyl]amino]-1-(1H-indol-3-ylmethyl)-1-methyl-2-oxoethyl]carbamic acid, 101. [R-(R*,R*)]-3-[[2-[[3-(1H-indol-3-yl)-2-methyl-1-oxo-2-[[(tricyclo[3.3.1.1$^{3,7}$]dec-2-yloxy) carbonyl]amino]propyl]amino]-1-phenylethyl]amino]-3-oxopropanoic acid, 102. [R-(R*,S*)]-3-[[2-[[3-(1H-indol-3-yl)-2-methyl-1-oxo-2-[[(tricyclo[3.3.1.1$^{3,7}$]dec-2-yloxy) carbonyl]amino]propyl]amino]-3-phenylpropyl]amino]-3-oxopropanoic acid, 103. [R-[R*,S* [(E)]]-4-[[2-[[3-(1H-indol-3-yl)-2-methyl-2-[[(bicyclo [3.3.1 ]non-9-yloxy) carbonyl]amino]-1-oxopropyl]amino]-3-phenylpropyl]amino]-4-oxo-2-butenoic acid, 104. [R-[R*,S*)]-5-[[2-[[3-(1H-indol-3-yl)-2-methyl-1-oxo-2-[[(tricyclo[3.3.1.1$^{3,7}$ ]dec-2-yloxy) carbonyl]amino]propyl]amino]-3-phenylpropyl]amino]-5-oxopentanoic acid, 105. ethyl[R-(R*,S)]-[[2-[[3-(1H-indol-3-yl)-2-methyl-1-oxo-2-[[(tricyclo[3.3.1.1$^{3,7}$ ]dec-2-yloxy)-carbonyl]amino]propyl]amino]-3-phenylpropyl]sulfinyl]acetate, 106. [R-(R*,R*-(E)]]-4-[[2-[[3-(1H-indol-3-yl)-2-methyl-1-oxo-2-[[(tricyclo[3.3.1.1$^{3,7}$]dec-2yloxy)carbonyl]amino]propyl]amino]-1-phenylethyl ]amino]-4-oxo-2-butenoic acid, 107. [R-(R*,S*)]—N-[3-[[3-(1H-indol-3-yl)-2-methyl-1-oxo-2-[[(tricyclo[3.3.1.1$^{3,7}$]dec-2-yloxy) carbonyl]amino]propyl]amino]-1-oxo-4-phenylbutyl]-β-alanine, 108. N-[N-[-methyl—N-[(tricyclo[3.3.1.1$^{3,7}$]dec-2-yloxy)carbonyl]-D-tryptophyl]-L-phenylalanyl]-L-alanine, 109. [R-R*,S*)]-3-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]thio]propanoic acid, 110. [R-(R*,S*)]-[[2-[[2-[3-(1H-indol-3-yl)-2-methyl-1-oxo-2-[[(tricyclo[3.3.1.1$^{3,7}$]dec-2-yloxy) carbonyl]amino]propyl]amino]-3-phenylpropyl]thio]acetic acid, 111. [R-(R*,S*)]-β-[[3-(1H-indol-3-yl)-2-methyl-1-oxo-2-[[(tricyclo[3.3.1.1$^{3,7}$ ]dec-2-yloxy) carbonyl]amino]propyl]amino]benzenebutanoic acid, 112. tricyclo[3.3.1.1$^{3,7}$]dec-2-yl[R-(R*,S*)]-3-(1H-indol-3-ylmethyl)-3-methyl-4, 10-dioxo-6-(phenylmethyl)-11-oxa-8-thia-2,5-diazatridecanoic acid, 113. Carbamic acid, [2-[[1-(hydroxymethyl)-2-phenylethyl]amino]-1-methyl-1- [(1-methyl-1H-indol-3-yl)methyl]-2-oxoethyl]-, tricyclo[3.3.1.1$^{3,7}$]dec-2-yl ester, JR-(R*,S*)]-, 114. Glycine, N-[3-(1H-indol-3-yl)-2-methyl-1-oxo-2-[[(tricyclo[3.3.1.1$^{3,7}$]dec-2-yloxy) carbonyl]amino]propyl]-N-(2-phenylethyl)—, (±)-, 115. Glycine, N-[3-(1H-indol-3-yl)-2-methyl-1-oxo-2-[[(tricyclo[3.3.1.1$^{3,7}$]dec-2-yloxy) carbonyl]amino]propyl]-N-(2-phenylethyl)-, methyl ester, (±)-, 116. Methyl (±)-7-[[3-(1H-indol-3-yl)-2-methyl-1-oxo-2-[[(tricyclo[3.3.1.1$^{3,7}$]dec-2-yloxy) carbonyl]amino]propyl](2-phenylethyl)amino]heptanoate, 117. (±)-7-[[3-(1H-indol-3-yl)-2-methyl-1-oxo-2-[[tricyclo[3.3.1.1$^{3,7}$ ]dec-2-yloxycarbonyl]amino]propyl](2-phenylethyl)amino]heptanoic acid, 118. Carbamic acid, [2-[[2-(1-cyclohexen-1-yl) ethyl]amino]-1-(1H-indol-3-ylmethyl)-1-methyl-2-oxoethyl]-, (R)-, 119. Carbamic acid, [1-(1H-indol-3-ylmethyl)-1-methyl-2-oxo-2-[[2-(2-pyr i diny 1 ) ethyl]amino]ethyl]-, tricyclo[3.3.1.1$^{3,7}$]dec-2-yl ester, (R)-, 120. Benzenebutanoic acid, 4-amino--[[3-(1H-indol-3-yl)-2-methyl-1-oxo-2-[[(tricyclo[3.3.1.1$^{3,7}$]dec-2-yloxy)carbonyl]amino]propyl]amino]-, [R-(R*,S*)]-, 121. Acetic acid, [[3-[[3-(1H-indol-3-yl)-2-methyl-1-oxo-2-[[(tricyclo[3.3.1.1$^{3,7}$]dec-2-yloxy) carbonyl]amino]propyl]amino]-2-phenylpropyl]thio]- (TRP center is R, other center is RS), 122. 12-oxa-9-thia-2,5-diazatetradecanoic acid, 3-(1H-indol-3-ylmethyl)-3-methy 1-4,11-dioxo-7-phenyl-, tricyclo[3.3.1.1$^{3,7}$]dec-2-yl ester (TRP center is R, other center is RS), 123. Benzenebutanoic acid, γ-[[[3-(1H-indol-3-yl)-2-methyl-1-oxo-2-[[(tricyclo[3.3.1.1$^{3,7}$]dec-2-yloxy)carbonyl]amino]propyl]amino]methyl]-(TRP center is R, other center is RS), 124. 2-pentenoic acid, 5-[[3-(1H-indol-3-yl)-2-methyl-1-oxo-2-[[(tricyclo[3.3.1.1$^{3,7}$ ]dec-2-y 1 oxy ]carbon yl]amino]propyl]amino]-4-phenyl-, methyl ester (TRP center is R, other center is RS, double bond is (E)), 125. Benzenebutanoic acid, γ-[[[3-(1H-indol-3-yl)-2-methyl-1-oxo-2-[[(tricyclo[3.3.1.1$^{3,7}$]dec-2-yloxy)carbonyl]amino]propyl]amino]methyl]-, methyl ester (TRP center is R, other center is RS), 126. Butanoic acid, 4-[[2-[2-[[3-(1H-indol-3-yl)-2-methyl-1-oxo-2-[[(tricyclo[3.3.1.1$^{3,7}$]dec-2-yloxy)carbonyl]amino]propyl]amino]ethyl]phenyl]amino]-4-oxo-, (R)—, 127. Carbamic acid, [1-(1H-indol-3-ylmethyl)-1-methyl-2-oxo-2-[[2-[[[(1H-1,2,4-triazol-5-ylthio)acetyl]amino]-2-phenylethyl]amino]ethyl]-, tricyclo-[3.3.1.1$^{3,7}$]dec-2-yl ester, [R-(R*,R*)]-, 128. Carbamic acid, [2-[[2-[[(1H-imidazol-2-ylthio)acetyl]amino]-2-phenylethyl]amino]-1-(1H-indol-3-ylmethyl)-1-methyl-2-oxoethyl]-, tricyclo[3.3.1.1$^{3,7}$]-dec-2-yl ester, [R-(R*,R*)]-, 129. Butanoic acid, 4-[[2-[[3-(1H-indol-3-yl)-2-methyl-1-oxo-2-[[(tricyclo[3.3-1.1$^{3,7}$]dec-2-yloxy)carbonyl]amino]propyl]amino]-1-phenylethyl]amino]-4-oxo-, (Phenyl center R, other center S or R) (Diastereomer II), 130. Butanoic acid, 4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxo- (Phenyl center R, other center R or S) (Diastereomer I), 131. 13-oxa-2,5,8-triazatetradecanoic acid, 3-(1H-indol-3-ylmethyl)-3-methyl-4,9,12-trioxo-7,14-diphenyl-, tricyclo[3.3.1.1$^{3,7}$]dec-2-yl ester (Phenyl center is R, other center is S or R) (Diastereomer 2), 132. 13-oxa-2,5,8-triazatetradecanoic acid, 3-(1H-indol-2-ylmethyl)-3-methyl-4, 9, 12-trioxo-7,14-diphenyl-, tricyclo[3.3.1.1$^{3,7}$]dec-2-yl ester (Phenyl center is R, other center is R or S) (Diastereomer 1), 133. Carbamic acid, [2-[[1-(hydroxymethyl)-2-phenylethyl]amino]-1-(1H-indol -2-ylmethyl)-1-methyl-2-oxoethyl]-, tricyclo[3.3.1.1$^{3,7}$]dec-2-yl ester (Hydroxymethyl center is S, other center is R or S) (Diastereomer 1), 134. Carbamic acid, [2-[[1-(hydroxymethyl)-2-phenylethyl]amino]-1(1H-indol -2-ylmethyl)-1-methyl-2-oxoethyl]-, tricyclo[3.3.1.1$^{3,7}$]dec-2-yl ester (Hydroxymethyl center is S, other center is S or R) (Diastereomer 2), and 135. Carbamic acid, [1-methyl-i-[[1-[(4-methylphenyl)sulfonyl]-1H-indol-2-yl]methyl]-2-oxo-2-[(2-phenylethyl)amino]ethyl], tricyclo[3.3.1.1$^{3,7}$]dec-2-yl ester, (±)-.

In addition to the compounds above the compounds of the present invention include compounds of formula I wherein the indole moiety is a 2-indolyl.

The compounds include solyates and hydrates and pharmaceutically acceptable salts of the compounds of formula I.

Preferred pharmaceutically acceptable salts are benzathine, chloroprocaine, choline, diethanolamine, ethylenediamine, meglumine, procaine, aluminum, calcium, lithium, magnesium, potassium, sodium, zinc, diethylamine, and tromethane.

Especially preferred pharmaceutically acceptable salts are N-methylglucamine and sodium.

The compounds of the present invention can have multiple chiral centers including those designated in the above formula I by an † ‡ ∗ depending on their structures. For example, when R$^3$ taken with R$^{12}$ and R$^4$ taken with R$^{13}$ form double bonds to these carbon atoms they are no longer chiral. In addition, centers of asymmetry may exist on substituents R$^1$, R$^9$, R$^3$, R$^4$ and/or Ar. In particular the compounds of the present invention may exist as diastereomers, mixtures of diastereomers, or as the mixed or the individual optical enantiomers. The present invention contemplates all such forms of the compounds. The mixtures of diastereomers are typically obtained as a result of the reactions described more fully below. Individual diastereomers may be separated from mixtures of the diastereomers by conventional techniques such as column chromatography or repetitive recrystallizations. Individual enantiomers may be separated by convention method well known in the art such as conversion to a salt with an optically active compound, followed by separation by chromatography or recrystallization and reconversion to the nonsalt form.

The compounds of the present invention can be formed by coupling individual substituted -amino acids by methods well known in the art. (See, for example, standard synthetic methods discussed in the multi-volume treatise "The Peptides, Analysis, Synthesis, Biology," by Gross and Meienhofer, Academic Press, New York.) The individual substituted alpha amino acid starting materials are generally known or, if not known, may be synthesized and, if desired, resolved by methods within the skill of the art. (Synthesis of racemic [DL]-α-methyl tryptophan methyl ester—see Braa, M. F., et al., *J. Heterocyclic Chem.*, 1980, 17:829.)

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5 to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active component with encapsulating material as a carrier providing a capsule in which the active component (with or without other carriers) is surrounded by a carrier which ie thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The dipeptoids, their pharmaceutically acceptable salts, hydrates, and solyates are administered to mammals, e.g., humans.

The diagnosis of the group of disorders covered herein is the predominant disturbance as in Panic Disorder as in the third edition-revised of the *Diagnostic and Statistical Manual Of Mental Disorders* (DSM-111-R), published by the American Psychiatric Association (1987).

Pharmaceutical Formulations

In the following examples of pharmaceutical formulations according to the present invention, unless otherwise indicated, the term "Active Ingredient" represents a dipeptoid of the invention hereinbefore defined or a pharmaceutically acceptable salt thereof. The dose represents that appropriate for the base; if a salt is used the dose should of course be increased appropriately.

EXAMPLE 1

| Tablet | |
|---|---|
| Ingredient | Amount per tablet (mg) |
| Active Ingredient* | 60.0 |
| Lactose | 125.0 |
| Corn Starch | 50.0 |
| Polyvinylpyrrolidone | 3.0 |
| Stearic acid | 1.0 |
| Magnesium stearate | 1.0 |

*[R-(R*,R*)]-4-[[2-[[3-(1H-indol-3-yl)-2-methyl-1-oxo-2-[[tricyclo[3.3.1.1$^{3.7}$]dec-2-yloxy)carbonyl]amino]propyl]amino]-1-phenylethyl]amino]-4-oxobutanoic acid

EXAMPLE 2

| Capsule | |
|---|---|
| Ingredient | Amount per capsule (mg) |
| Active Ingredient* | 60.0 |
| Lactose | 174.0 |
| Corn Starch | 174.0 |
| Stearic acid | 2.0 |

*[R-(R*,R*)]-4-[[2-[[3-(1H-indol-3-yl)-2-methyl-1-oxo-2-[[tricyclo[3.3.1.1$^{3.7}$]dec-2-yloxy)carbonyl]amino]propyl]amino]-1-phenylethyl]amino]-4-oxobutanoic acid

EXAMPLE 3

| Ampoule | |
|---|---|
| Ingredient | Amount per ampoule |
| Active Ingredient* | 60.0 mg |
| Water for injection, q.s. | 1.0 mL |

*[R-(R*,R*)]-4-[[2-[[3-(1H-indol-3-yl)-2-methyl-1-oxo-2-[[tricyclo[3.3.1.1$^{3.7}$]dec-2-yloxy)carbonyl]amino]propyl]amino]-1-phenylethyl]amino]-4-oxobutanoic acid

EXAMPLE 4

| Suppository | |
|---|---|
| Ingredient | Amount per suppository |
| Active Ingredient* | 60.0 mg |
| Theobroma oil (cocoa butter), q.s. | 2.0 g |

*[R-(R*,R*)]-4-[[2-[[3-(1H-indol-3-yl)-2-methyl-1-oxo-2-[[tricyclo[3.3.1.1$^{3.7}$]dec-2-yloxy)carbonyl]amino]propyl]amino]-1-phenylethyl]amino]-4-oxobutanoic acid

I claim:

1. A method of treating a panic disorder in a human who has been identified as exhibiting panic disorder symptoms which comprises administering to said human a therapeutically effective amount of a compound of formula

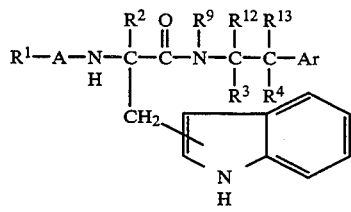

I or a pharmaceutically acceptable salt thereof wherein: a cyclo- or polycycloalkyl hydrocarbon of from three to twelve carbon atoms with from zero to four substituents, each independently selected from the group consisting of: a straight or branched alkyl of from one to six carbon atoms, halogen, CN, OR* SR*, $CO_2R^*$, $CF_3$, $NR^5R^6$ or $(CH_2)_nOR^5$ wherein R* is hydrogen, straight or branched alkyl of from one to six carbon atoms, $R^5$ and $R^6$ are each independently hydrogen or alkyl of from one to six carbon atoms; and n is an integer from zero to six;

A is $(CH_2)_nCO-$, $-SO_2-$, $-S(=O)-$, $-NH-CO-$,

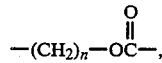

$-SCO-$, $O-(CH_2)_nCO-$ or $-HC=CHCO-$ wherein n is an integer from zero to six;

$R_2$ is a straight or branched alkyl of from one to six carbon atoms, $-HC=CH_2$, $-C\equiv CH$, $-C-2-CH=CH_2$, $-CH_2C\equiv CH$, $-(CH_2)_nAr$, $-(CH_2)_nOR^*$, $-(CH_2)_nOAr$, $-(CH_2)_nCO_2R^*$, or $-(CH_2)_nNR^5R^6$ wherein n R' $R^5$ and $R^6$ are as defined above and Ar is as defined below;

$R^3$ and $R^4$ are each independently selected from hydrogen $R^2$ and $-(CH_2)_{n'}$ $-B-D$ wherein n' is an integer of from zero to three;

B is a bond, $-OCO(CH_2)_n-$,
$-O(CH_2)_n-$,
$-SO_2NH(CH_2)_n-$,
$-NHSO_2(CH_2)_n$,
$-NOCO(CH_2)_n-$,
$CONH(CH_2)_n-$,
$NHCOCH=CH-$,
$-COO(CH_2)_n-$,
$-CO(CH_2)_n-$,
$-S-(CH_2)_n-$,
$-SO(CH_2)_n-$,
$-SO_2(CH_2)_n-$,

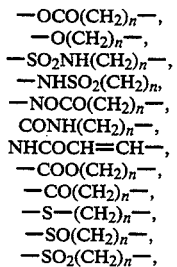

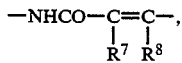

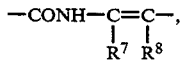

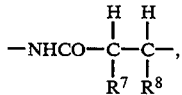

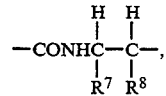

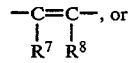

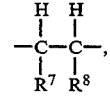

wherein $R^7$ and $R^8$ are independently selected from hydrogen and $R^2$ or together form a ring $(CH_2)_m$ wherein m is an integer of from 1 to 5 and n is as defined above;

D is
  $-COOR'$,
  $'CH_2OR^*$,

—CHR²OR*,
—CH₂SR*,
—CR²SR*,
—CONR⁵R⁶,
—CN,
—NR⁵R⁶,
—OH,
—H, and acid replacements:

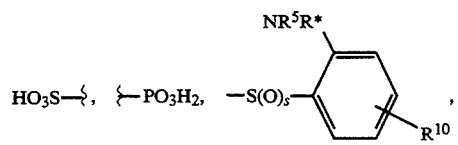

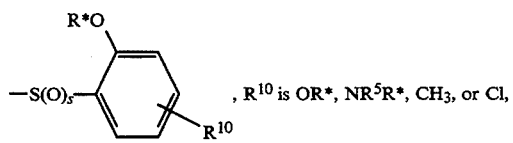, R¹⁰ is OR*, NR⁵R*, CH₃, or Cl, s is an integer of from 0 to 2
wherein R*, R², R⁵, R⁶ and R¹⁰ are as defined above; R⁹ is H, or a straight or branched alkyl of from one to six carbon atoms, —(CH₂)ₙCO₂R*, (CH₂)ₙOAr', (CH₂)ₙAr', (CH₂)ₙNR⁵R⁶, wherein n, R*, R⁵, and R⁶ are as defined above or taken from R³ and Ar' is taken from Ar as defined below;
R¹² and R¹³ can each be independently hydrogen in which case the carbon atom to which it is attached is a chiral center, or can each be taken with R³ and R⁴ respectively to form a moiety doubly bonded to the carbon atom in which case the carbon atom is not chiral; and
Ar is a mono- or polycyclic unsubstituted or substituted carbo- cyclic aromatic or hydroaromatic moiety.

2. A method according to claim 1 wherein the amount is 0.25 to 15 mg/kg of body weight.

3. A method according to claim 1 wherein the amount is 1 to 10 mg/kg of body weight.

4. A method according to claim 1 wherein in the compound of formula I the cycloalkyl or polycycloalkyl has from about six to ten carbon atoms unsubstituted or substituted with one or more substituents, each substituent selected independently from: methyl, fluorine, chlorine, and bromine 5. A method according to claim 1 wherein in the compound of formula I R¹ is cycloalkyl or polycycloalkyl wherein the polycycloalkyl is selected from the group consisting of

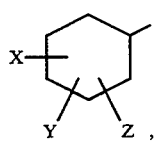

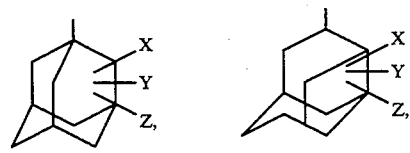

-continued

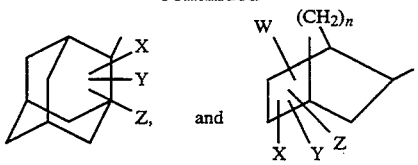

wherein W, X, Y, and Z are each independently hydrogen, a straight or branched alkyl of from one to six carbon atoms CF₃, NR⁵R⁶, —(CH₂)ₙCO₂R*, CN, F, Cl, Br, OR*, SR*, wherein R*, R⁵ and R⁶ are as defined in claim 1 and n is an integer of from 1 to 3;
A is —NHCO—, OC(=O)—, —SO₂—, —S(=O)—, —SCO— or —CH₂CO—; and
Ar is an unsubstituted or substituted phenyl whose substituents if any are each independently hydrogen, fluorine, chlorine, bromine, iodine, methyl, methoxy, trifluoromethyl nitro, OH, NH₂, OCF₃, NHCOCH₂CH₂CO₂H, or CH₂CH₂CO₂H.

6. A method according to claim 1 wherein in the compound of formula I:
R¹ is 2-adamantyl or 1-(S)-2-endobornyl;
A is —NHCO—, —OCO—, —SO₂—, —S(=O)— or —CH₂CO—;
R² is —CH₃, —CH₂CO₂H or —CH₂C≡CH
R³ is —(CH₂)ₙ,—B—D or H;
R⁴ is —(CH₂)ₙ—B—D or H; and
R⁹ is hydrogen or methyl.

7. A method according to claim 1 wherein in the compound of formula I:
R¹ is 2-adamantyl, 1-(S)-2-endobornyl, or 2-methyl cyclohexyl ;
A is —OC(=O)—;
R² is —CH₃;
R³ is H, CH₂OH, CH₂OCOCH₂CH₂CO₂H, CH₂OCOCH=CHCO₂H, CH₂NHCOCH₂CH₂CO₂H, CH₂NHCOCH=CHCO₂H, or CH₂CO₂H;
R⁴ is H, —CH₂SCH₂CO₂H, —CH₂SCH₂CH₂CO₂H, —NHCOCH=CHCO₂H, —NHCOCH₂CH₂CO₂H in the (D) configuration, or NHCOCH=CHCO₂H in the (D) configuration).

8. A method according to claim 1 wherein the compound is selected from:
(±)-trans-2-chlorocyclohexyl[1-(1H-indol-3-ylmethyl)-1-methyl-2-oxo-2-[(2-phenylethyl)amino]ethyl]carbamate;
2-chlorocyclohexyl[2-[[1-(hydroxymethyl)-2-phenylethyl]-amino]-1-(1H-indo 1-3-ylmethyl)-1-methyl-2-oxoethyl]-carbamate;
2-[[2-[[[(2-chlorocyclohexyl)oxy]carbonyl]amino]-3-(1H-indol-3-yl)-2-methyl-1-oxopropyl]amino]-3-phenylpropyl butanedioate;
2-[[2-[[[(2-methylcyclohexyl)oxy]carbonyl]amino]-3-(1H-indol-3-yl)-2-methyl-1-oxopropyl]amino]-3-phenylpropyl butanedioate;
(±)-tricyclo[3.3.1.1³,⁷]dec-2-yl[1-(1H-indol-3-ylmethyl)-1-methyl-2-oxo-2-[(2-phenylethyl)amino]-ethyl]carbamate;
(+) or (−)-2-chlorocyclohexyl[1-(1H-indol-3-ylmethyl)-1-methyl-2-oxo-2-[(2-phenylethyl)amino]ethyl]carbamate;
tricyclo[3.3.1.1³,⁷]dec-2-yl[2-[[1-(hydroxymethyl)-2-phenylethyl]amino]-1-(1H-indol-3-ylmethyl)-1-methyl-2-oxoethyl]carbamate;

2-[[3-(1H-indol-3-yl)-2-methyl-1-oxo-2-[[(tricyclo-[3.3.1.1$^{3,7}$]dec-2-yloxy)carbonyl]amino]propyl-]amino]-3-phenylpropyl butanedioate;

[1S-[1α,2β[S*(S*)],4α]]-4-[[2-[[3-(1H-indol-3-yl)--2-methyl-1-oxo-2-[[[(1,7,7-trimethylbicyclo[2.2.1-]hept-2-yl)oxy]carbonyl]amino]propyl]amino]-1-phenylethyl]amino]-4-oxobutanoic acid;

[R-[R*,S*-(E)]]-4-[[2-[[3-(1H-indol-3-yl)-2-methyl-1-oxo-2-[[tricyclo[3.3.1.1$^{3,7}$]dec-2-yloxy)carbonyl-]amino]-propyl]amino]-3-phenylpropyl]amino]-4-oxo-2-butenoic acid;

[R-(R*,S*)]-4-[[2-[[3-(1H-indol-3-yl)-2-methyl-1-oxo-2-[[(tricyclo[3.3.1.1$^{3,7}$]dec-2-yloxy)carbonyl-]amino]-propyl]amino]-3-phenylpropyl]amino]-4-oxo-butanoic acid;

[R-(R*,S*)]-4-[[2-[[3-(1H-indol-3-yl)-2-methyl-1-oxo-2-[[(tricyclo[3.3.1.1$^{3,7}$]dec-2-yloxy)carbonyl-]amino]-propyl]amino]-3-phenylpropyl]amino]-4-oxo-butanoic acid; (R)-tricyclo[3.3.1.1$^{3,7}$]dec-2-yl[1-(1H-indol-3-ylmethyl)-1-methyl-2-[methyl(2-phenylethyl)amino]-2-oxoethylcarbamate,

[R-(R*,S*)]-2-[[2-[[3-(1H-indol-3-yl)-2-methyl-1-oxo-2-[[(tricyclo[3.3.1.1$^{3,7}$]dec-2 -yloxy)carbonyl-]amino]-propyl]amino]-3phenylpropyl]sulfinyl]acetic acid;

[R-(R*,S*)]-[[2-[[2-[3-(1H-indol-3-yl)-2-methyl-1-oxo-2-[[(tricyclo[3.3.1.1$^{3,7}$]dec-2-yloxy)carbonyl-]amino]-propyl]amino]-3-phenylpropyl]thio]acetic acid;

[R-(R*,S*)]-[[2-[[3-(1H-indol-3-yl)-2-methyl-1-oxo-2-[[(tricyclo[3.3.1.1$^{3,7}$]dec-2-yloxy) carbonyl]amino]-propyl]amino]-3-phenylpropyl]sulfinyl]acetic acid, ethyl ester;

[R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]-propyl]amino]-3-phenylpropyl]sulfonyl]acetic acid;

[R-[R*,R*-(E)]]-4-[[2-[[3-(1H-indol-3-yl)-2-methyl-1-oxo-2-[[(tricyclo[3.3.1.1$^{3,7}$]dec-2-yloxy)carbonyl-]amino]-propyl]amino]-1-phenylethyl]amino]-4-oxo-2-butenoic acid;

[R-(R*,S*)]-[[2-[[2-[3-(1H-indol-3-yl)-2-methyl-1-oxo-2-[[(tricyclo[3.3.1.1$^{3,7}$]dec-2-yloxy)carbonyl-]amino]-propyl]amino]-3-phenylpropyl]thio]acetic acid;

[1S-[1α,2β[S*[S*(E)]],4α]]-4-[[2-[[3-(1H-indol-3-yl)--2-methyl-1-oxo-2-[[[(1,7,7-trimethylbicyclo[2.2.1-]hept-2-yl)oxy]carbonyl]amino]propyl]amino]-1-phenylethyl]amino]-4-oxo-2-butenoic acid, methyl ester, (bicyclo system is 1S-endo);

[1S-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl-]amino]-1-phenylethyl]amino]-4-oxo-2-butenoic acid (bicyclo system is 1S-endo);

[R-(R*,R*)]-3-[[2-[[3-(1H-indol-3-yl)-2-methyl-1-oxo-2-[[(tricyclo[3.3.1.1$^{3,7}$]dec-2 -yloxy) carbonyl]amino]-propyl]amino]-1-phenylethyl]amino]-3-oxopropanoic acid;

[R-(R*,S*)]-3-(1H-indol-3-ylmethyl)-3-methyl-4,10-dioxo-6-(phenylmethyl)-11-oxo-8-thia-2,5-diaza-tridecanoic acid, tricyclo[3.3.1.1$^{3,7}$]-dec-2-yl or ester;

[R-(R*,S*)]-β-[[3-(1H-indol-3-yl)-2-methyl-1-oxo-2-[[(tricyclo[3.3.1.1$^{3,7}$]dec-2-yloxy)carbonyl]amino]-propyl]amino]benzenebutanoic acid;

[R-(R*,S*)]-β-[[3-(1H-indol-3-yl)-2-methyl-1-oxo-2[[(tricyclo[3.3.1.1$^{3,7}$]dec-2-yloxy)carbonyl-]amino]propyl]amino]-4-iodobenzenebutanoic acid, where the iodo group may be I-125 or I-127;

[R-(R*,S*)]—N-[3-[[3-(1H-indol-3-yl)-2-methyl-1-oxo-2-[[(tricyclo[3.3.1.1$^{3,7}$]dec-2yloxy)carbonyl-]amino]-propyl]amino]-4-phenylbutyl]glycine; and

[R-[R*,S*-(E)]]-4-[[2-[[3-(1H-indol-3-yl)-2-methyl-2-[[(bicyclo [3.3.1 ]non-9-yloxy) carbonyl]amino]-1-oxopropyl]amino]-3-phenylpropyl]amino]4-oxo-2-butenoic acid.

9. A method of treating panic disorder in a human who has been identified as exhibiting panic disorder symptoms which comprises administering to said human a therapeutically effective amount of [R-(R*,R*)]-4-[[2-[[3-(1H-indol-3-yl)-2-methyl-1-oxo-2-[[(tricyclo[3.3.1.1$^{3,7}$]dec-2-yloxy) carbonyl]amino]-propyl]amino]-1-phenylethyl]amino-4-oxobutanoic acid, or a pharmaceutically acceptable salt thereof.

* * * * *

UNITED STATES PATENT AND TRADEMARK OFFICE
CERTIFICATE OF CORRECTION

PATENT NO. : 5,451,602
DATED : September 19, 1995
INVENTOR(S) : Woodruff

It is certified that error appears in the above-indentified patent and that said Letters Patent is hereby corrected as shown below:

On the Title page, item [54] and column 1, line 3, change "ATTCKS" to --ATTACKS--.

Column 23, line 65, after the colon insert --$R^1$ is--.

Column 24, line 19, at the beginning of the line insert --H-- to read $H_2$.

Column 24, line 19, in the second word, delete " = " and insert instead -- ≡ --.

Column 24, line 24, after " drogen " insert comma.

Column 24, line 32, the first " O " should be -- H --.

Column 24, last line, delete " ' " at the beginning of the line and insert instead -- - --.

Column 26, line 29, delete subscript " n " and insert instead subscript -- n' --.

Column 26, line 51, close up space and change the " 1 " to -- l -- so that word reads -- indol --.

Column 27, line 16 through the word " acid: " on line 19, delete as it is a duplicate.

UNITED STATES PATENT AND TRADEMARK OFFICE
CERTIFICATE OF CORRECTION

PATENT NO. : 5,451,602
DATED : September 19, 1995
INVENTOR(S) : Woodruff

It is certified that error appears in the above-indentified patent and that said Letters Patent is hereby corrected as shown below:

Column 27, line 19, the " (R)... " should start a new paragraph.

Column 27, line 24, insert hyphen after the " 3 ".

Column 27, line 26, delete the second " [[2- ".

Column 27, line 26, before the " [3 " insert -- [ --.

Column 27, line 27, after the " ) " insert -- ] --.

Column 27, line 28, delete the word " thio " and insert instead -- sulfonyl --.

Column 28, line 29, insert -- - -- between the " 2 " and " yloxy ".

Signed and Sealed this

Nineteenth Day of March, 1996

Attest:

BRUCE LEHMAN

Attesting Officer     Commissioner of Patents and Trademarks